(12) United States Patent
Knodel et al.

(10) Patent No.: US 8,152,794 B2
(45) Date of Patent: Apr. 10, 2012

(54) ENDOSCOPIC INSTRUMENT

(75) Inventors: Frank Knodel, Knittlingen (DE);
Ludwig Bonnet, Knittlingen (DE);
Stefan Gille, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 1519 days.

(21) Appl. No.: 11/609,376

(22) Filed: Dec. 12, 2006

(65) Prior Publication Data

US 2007/0135807 A1    Jun. 14, 2007

(30) Foreign Application Priority Data

Dec. 12, 2005   (DE) .................... 20 2005 019 811 U

(51) Int. Cl.
*A61B 18/20*    (2006.01)
(52) U.S. Cl. ............................................. 606/1; 606/15
(58) Field of Classification Search ................. 604/165, 604/167; 606/15; 600/206
See application file for complete search history.

(56) References Cited

U.S. PATENT DOCUMENTS

| 5,028,117 | A |   | 7/1991 | Muhlenkamp-Becker |         |
|-----------|---|---|--------|-------------------|---------|
| 5,178,150 | A |   | 1/1993 | Silverstein et al.|         |
| 5,738,631 | A | * | 4/1998 | Konstorum         | 600/148 |
| 5,800,342 | A | * | 9/1998 | Lee et al.        | 600/114 |
| 5,840,013 | A | * | 11/1998| Lee et al.        | 600/114 |
| 6,458,077 | B1| * | 10/2002| Boebel et al.     | 600/154 |
| 6,886,267 | B1| * | 5/2005 | Karwowski et al.  | 33/613  |
| 7,122,017 | B2| * | 10/2006| Moutafis et al.   | 604/22  |
| 2005/0267458 | A1 | * | 12/2005 | Paul et al.   | 606/41  |
| 2006/0036164 | A1 | * | 2/2006  | Wilson et al. | 600/424 |
| 2006/0089660 | A1 | * | 4/2006  | Saeed et al.  | 606/139 |

FOREIGN PATENT DOCUMENTS

DE    198 26 311 C2    3/2003
WO    2004/096295 A2   11/2004

OTHER PUBLICATIONS

"Laserscope Healing with Light", Literature re: Products and Overview, http://www.laserscope.com, pp. 1-7 (2005).

* cited by examiner

*Primary Examiner* — Henry M Johnson, III
(74) *Attorney, Agent, or Firm* — Panitch Schwarze Belisario & Nadel LLP

(57) ABSTRACT

An endoscopic instrument includes a shank (2) having at least one guide channel (4, 4') for a laser probe (8), and a flexible narrowing provided in a section of the guide channel (4) connecting to its distal end. The flexible narrowing allows a clear diameter of the guide channel (4, 4') to be changed in at least one direction.

13 Claims, 3 Drawing Sheets

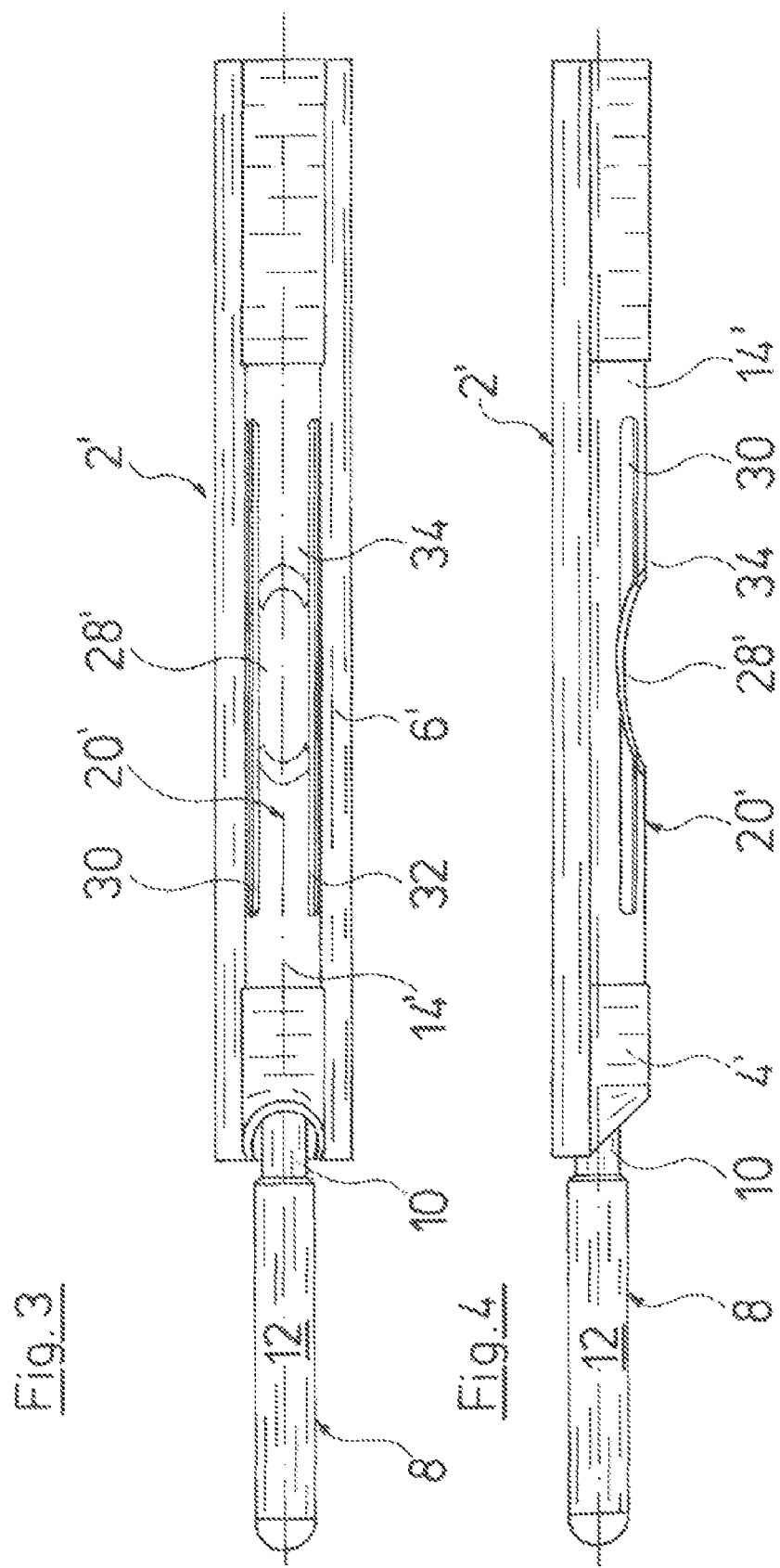

ENDOSCOPIC INSTRUMENT

BACKGROUND OF THE INVENTION

The invention relates to an endoscopic instrument.

Endoscopic instruments are known, which comprise a hollow shank, through which a laser probe may be guided to a field of operation for removing body tissue. The laser probes in these instruments may be moved from a non-active position, in which the laser head is arranged within the hollow shank, into a working position in which the laser head protrudes at the distal shank end. In order to prevent an undesired axial shifting of the laser probe, it is usual to fix the fiber leads of these laser probes in a handle arranged on the proximal end of the hollow shank. Particularly when the part of the laser probe arranged within the hollow shank in the working position of the laser probe, usually its fiber lead, has a significantly smaller cross section compared to the guide channel formed by the hollow shank, these laser probes tend to oscillate within the hollow shank on account of the flexibility of the fiber leads. This may lead to an uncontrolled moving around of the laser beam upon removal of the tissue.

BRIEF SUMMARY OF THE INVENTION

Against this background, it is an object of the present invention to provide an endoscopic instrument which, with a simple construction, permits a more accurate alignment of the laser beam.

This object is achieved by an endoscopic instrument according to the invention, which comprises a shank forming at least one guide channel for a laser probe, for example for removing body tissue. A flexible narrowing is provided in a section of the guide channel, which connects to the distal end, such that the narrowing enables the clear diameter of the guide channel to be changed in at least one direction.

The narrowing of the guide channel may be formed by a part of the guide channel itself, or by a separate component. A section of the inner wall, or a component forming the narrowing, i.e., a component forming this section of the inner wall, proceeding from the inner periphery of the guide channel, projects in at least one radial direction into the inside of the guide channel, whereby its cross-sectional diameter or its clear diameter is reduced at this location. Moreover, the component forming the narrowing, e.g., the section of the inner wall forming the narrowing, is so deformable on account of its flexible or elastic design, that the size of the narrowing, and thus also the clear diameter of the guide channel may be changed. Thus the radial extension of the guide channel in the region of the narrowing may be enlarged by way of exerting force on the narrowing. The flexibility of the section of the inner wall forming the narrowing thereby advantageously permits such a change in shape that the cross section of the guide channel required for the laser probe is made available.

The instrument according to the invention, on account of this design, permits the secure application of a large spectrum of different laser probes with regard to their geometric design. Thus on the one hand, with the instrument according to the invention, one may guide those laser probes through the shank to a field of operation, whose maximal cross section corresponds essentially to the inner cross section of the guide channel. On the other hand, the design according to the invention also permits laser probes with a cross section, which is relatively small in comparison to the inner cross section of the guide channel, to be fixed in a section at the distal end of the guide channel. Thus, the laser probe is given no freedom of movement transverse to its longitudinal extension. Accordingly, with the instrument according to the invention, unintended movements of the laser head, and thus a moving-around of the laser beam which this entails, are prevented or at least limited.

The invention is particularly advantageous for the guiding of those laser probes, whose laser head has a larger cross section compared to the fiber lead, in particular for so-called sidefire laser probes. With sidefire laser probes the exit of the laser beam, via a deflection prism arranged in the laser head, is effected essentially transverse to the longitudinal extension of the laser probe. With regard to the cross section of the fiber lead, this necessitates a significantly larger diameter of the laser head. Thus, it is possible with the instrument according to the invention to introduce a sidefire laser probe at the proximal end of a guide channel, to lead it through the complete guide channel. The laser head, with deformation of the narrowing, passes the section of the narrowing, and may be brought into a working position outside the shank. As soon as the laser head has passed the narrowing, the section of the inner wall forming the narrowing, or the component forming the narrowing, shapes back in the direction of the inside of the guide channel. This fixes the fiber lead, which is significantly slimmer compared to the laser head and thus compared to the guide channel, in the proximity of the distal end of the guide channel. Undesired vibrations of the laser head during the removal of body tissue are prevented or at least significantly reduced in this manner, so that the removal of tissue may be carried out in a more effective manner.

Advantageously, with the instrument according to the invention, at least one section of an inner wall of the guide channel is designed in a resilient manner transversely to its longitudinal axis. In particular, it is envisaged to design the section of the inner wall which forms the narrowing and protrudes into the inner lumen of the guide channel in a resilient manner. With a suitable dimensioning of this section, and the selection of a suitable spring-elastic material, it is possible to fix the part of the laser probe coming to abut on the narrowing, generally the fiber lead, in the region of the distal end of the guide channel with a non-positive fit. Thus, the laser probe may, for example, be fixed with a non-positive fit between a resiliently designed section of the inner wall of the guide channel, and a rigidly designed section of the guide channel lying diametrically opposite this section. Furthermore, the possibility also exists of providing several resiliently designed sections, which are distributed over the periphery of the guide channel and which all radially project in the direction of the center of the guide channel, in order to fix the laser probe between these sections, spaced from the inner wall of the guide channel in the region of the middle axis of the guide channel.

A spring element is preferably provided for forming the resiliently designed section, and this spring element is arranged on or in the guide channel. This spring element is designed in a manner such that in the unloaded condition, it projects into the guide channel and forms the narrowing. However, with a load acting on the spring element from the guide channel in the direction of the inner wall of the guide channel, the narrowing may be changed in shape, such that it forms a larger inner cross section, preferably essentially the whole inner cross section of the guide channel.

The spring element may, for example, be designed as a compression spring or as a leaf spring. The spring stiffness of the spring element is usefully designed such that on the one hand, a laser probe with a cross section which is significantly smaller with respect to the inner cross section of the guide channel, may be fixed securely in the guide channel transversely to its longitudinal extension. On the other hand, the narrowing may be deformed in a simple manner in the direction of the inner wall of the guide channel with a movement of the laser probe in the longitudinal direction of the guide channel, by a cross-sectional expansion of a laser probe or a laser probe whose cross section corresponds essentially to the inner cross section of the guide channel.

The spring element is advantageously formed by a section of the wall of the guide channel. This design, for example, is useful if at least a section of the guide channel is designed in a thin-walled manner, and the wall in this section consists of a spring-elastic material. In this case, no separate component is required for forming the narrowing in the guide channel.

Preferably, the wall of the guide channel comprises two slot-like (slotted) openings, which are aligned essentially parallel to the longitudinal axis of the guide channel. A section of the wall of the guide channel arranged between the openings is curved in an arch-like (arched) manner, such that it projects convexly into the inner lumen of the guide channel. The section of the wall of the guide channel, which is arranged between the openings, forms the spring element which, for example, is shaped by embossing this wall section, such that it narrows the inner cross section of the guide channel.

A preferred design of the instrument according to the invention envisages the spring element being designed as a leaf spring. Between two flat ends the leaf spring comprises a region curved in an arched manner, and is arranged in a manner such that the curved region, proceeding from the inner wall of the guide channel, projects convexly into the inner lumen of the guide channel.

The leaf spring is formed by a spring-elastic material, preferably a thin-walled metal strip whose two end sections, i.e., its regions which respectively border one end of the flat material, lie in a common plane, preferably in a flat manner. These two flat end sections may form the abutment surfaces of the leaf springs onto the wall of the guide channel. With the leaf spring, a middle region curves in an arched manner between the two end sections, preferably in the manner of a circular arc, out of the common plane of the end sections, wherein this region has its greatest curvature in its initial condition, thus unloaded. The leaf spring is preferably arranged in the guide channel, such that the flat end sections of the leaf springs bear on the wall of the guide channel, and the region of the leaf spring curved in an arched manner, proceeding from the wall of the guide channel, extends convexly, i.e. outwardly curved, in the direction of the diametrically opposite region of the wall. In this manner, the curved middle region of the leaf spring narrows the guide channel, wherein the narrowing is the largest in the region of the apex of the curvature. The radial distance between the apex of the curvature and the opposite wall determines essentially which laser probes may be fixed in the instrument according to the invention, transversely to their longitudinal extension. It is thus sufficient for the region of a laser probe situated in the working position, which comes to abut on the leaf spring, to have a diameter which is insignificantly larger than the radial distance between the apex of the curvature and the opposite wall of the guide channel.

The leaf spring may be arranged on the inner wall of the guide channel. Advantageously, the wall of the guide channel has an opening, through which the spring element is guided in a manner such that its curved region projects convexly into the inner lumen of the guide channel, and at least one flat end of the spring element is fastened on the outer wall of the guide channel. This design permits a particularly simple attachment of the leaf spring on the guide channel. Moreover, this design permits in the guide channel as flowing a transition as possible from the inner wall to the curved section of the spring element forming the narrowing.

The opening of the wall of the guide channel is provided in the region of the distal end of the guide channel. Its shape and size is determined essentially by the shape and size of the curved middle region of the leaf spring. Thus, the opening is usefully designed in a manner such that the middle region of the leaf spring, which is curved outwardly in a convex manner, may be completely pushed from the outer side of the guide channel though its wall, into the inner lumen of the guide channel. The two flat end sections of the leaf spring may come to abut on the outer wall of the guide channel in a flat manner. The fastening of the leaf springs is provided on the guide channel on at least one of these flat ends, the fastening being designed, for example, as a weld- or solder- or adhesive connection.

Further advantageously, the plane of curvature of the spring element extends in the direction of the longitudinal axis of the guide channel. For this purpose, the spring element forming the narrowing is arranged such that the clear diameter of the guide channel in the distal direction first continuously reduces in the longitudinal direction, proceeding from the full cross section on the proximal side of the spring element. After passing the apex of the curved middle region of the spring element, the narrowing continuously widens again in the further course, until the guide channel again has its initial cross section distally of the spring element. Abrupt cross-sectional transitions in the direction of the longitudinal extension of the guide channel are suitably avoided by this arrangement, and the axial guiding of a laser probe, and in particular the leading end of a laser probe past the spring element in the direction of the longitudinal axis, is simplified in this manner.

The endoscopic instrument according to the invention preferably forms a working insert for a resectoscope. Thus the instrument according to the invention may be inserted and fixed in the hollow shank of a resectoscope, which may be introduced into body openings, for example the urethra, and the laser probe may be guided via the instrument according to the invention, to the tissue to be removed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 a distal shank end of an endoscopic instrument in a plan view, with which the wall of the hollow shank forms a spring element; and FIG. 4 a lateral view of the distal shank end of an endoscopic instrument according to FIG. 3.

DETAILED DESCRIPTION OF THE INVENTION

Figure 1:
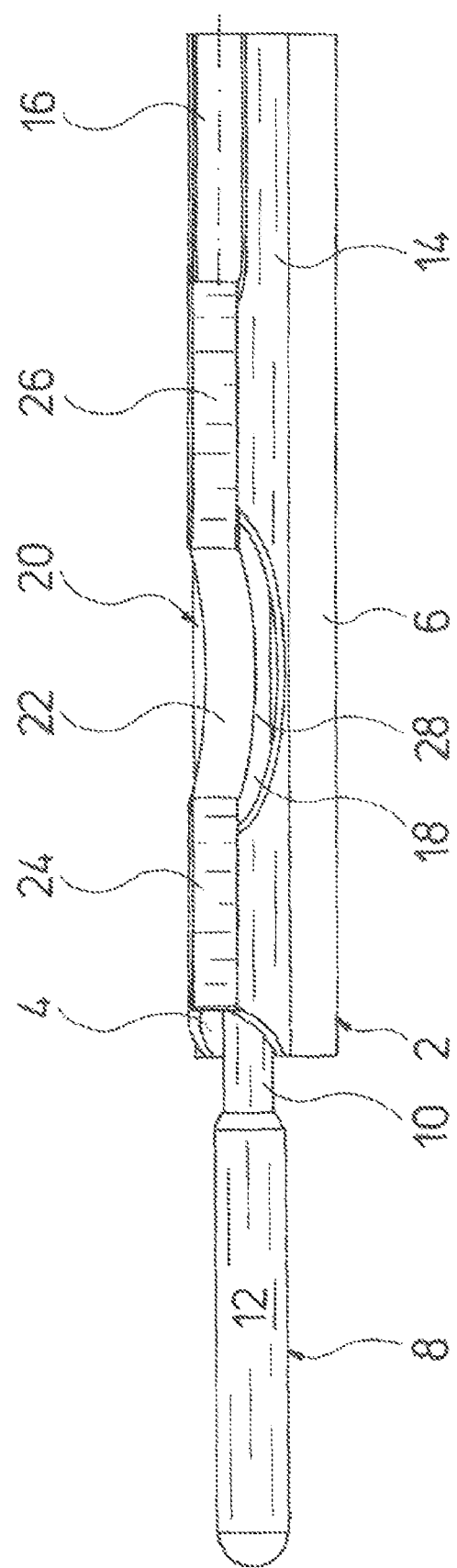
FIG. 1 is a longitudinal perspective view of a distal shank end of an endoscopic instrument according to the invention, with a laser probe guided therein.

The Figures show the distal end of a straight shank 2 of the instrument according to the invention. It is clear from FIG. 2 that the shank 2 forms a guide channel 4 and a guide rail 6 aligned parallel thereto. The guide channel 4 and the guide rail 6 are arranged in the shank 2 directly adjacent one another. The guide channel 4 serves for guiding a laser probe 8 for the removal of body tissue, while the guide rail 6 is provided for guiding observation optics (not shown in the Figures). The guide channel 4 and the guide rail 6 are designed in an open manner at their proximal end as well as at their distal end.

A laser probe 8 is guided in the guide channel 4. This laser probe 8 comprises an optical fiber lead 10 at whose distal end a laser head 12 is arranged. A beam exit opening (not shown) is provided on the laser head 12. The laser head 12 of the laser probe 8 in a plane normal to the longitudinal axis A has a cross section which is larger compared to the fiber lead 10. For tissue removal the laser probe 8 is introduced into the guide channel 4 at the proximal end of the shank 2 (not shown in the Figures), and is guided distally into the guide channel 4 until the laser head 12 protrudes at the distal end of the guide channel 4 or of the shank 2 in a working position, and thus the beam exit of the laser beam is effected outside the shank 2.

The cross section of the guide channel 4 is adapted to the cross section of the laser head 12 of the laser probe 10, and dimensioned such that the laser head 12 may be axially movably guided in the direction of the longitudinal axis A with slight play in the guide channel 4. The guide channel 4 is designed in an essentially tubular manner, wherein its wall 14 is flattened on the side distant from the guide rail 6, and forms the plane wall section 16.

The wall 14 of the guide channel 4, in a region connecting proximally to the distal end of the guide channel 4, comprises an opening 18 which ensures a free access to the inner lumen of the guide channel 4. Here, the opening 18 encompasses a section of the wall section 16, as well as a region of the wall 14 which is adjacent to the longitudinal sides in this section.

A spring element 20 engages into the inner lumen of the guide channel 4 at the opening 18. The spring element 20 is formed by a leaf spring 22. This leaf spring 22 is formed by a rectangular flat strip whose width corresponds essentially to the width of the plane wall section 16 of the guide channel 4, and with which the two end sections 24 and 26 are designed in a plane manner and lie in a common plane. A middle region 28 of the leaf spring 22 arranged between the end sections 24 and 26 curves in the manner of a circular arc transversely to this common plane of the end sections 24 and 26, so that the plane of curvature of the middle region 28 is directed normally to the plane of the end sections 24 and 26 and parallel to the longitudinal axis A.

The leaf spring 22 is arranged on the shank 2 in a manner such that the middle region 28 curved in an arch-like manner engages into the opening 18 and convexly into the inner lumen of the guide channel 4, and in this manner forms a narrowing in the guide channel 4, said narrowing reducing the clear diameter of the guide channel 4. Here, the plane end sections 24 and 26 lie on the wall section 16, which is likewise planar. The leaf spring 22 is connected to the wall section 16 in the region of the end sections 24 and 26.

The radius of curvature of the middle region 28 of the leaf spring 22 is dimensioned in a manner such that this middle region 28 projects so far into the inner lumen of the guide channel 4, that the clear diameter of the guide channel 4 is reduced in the region of the apex of the curvature to a value just below the diameter dimension of the fiber lead 10 of the laser probe 8. This, on account of the bias of the curved middle region 28, permits the fastening of the fiber lead 10 between the outer side of the middle region 28, on the guide channel side, and the region of the inner wall of the guide channel 4 lying opposite this middle region 28, with a non-positive fit and without play. In this manner, the freely oscillating length of the laser probe 8 may be reduced in the direction of its laser head 12, such that oscillations of the laser head 12 transverse to the longitudinal extension of the laser probe 8 are significantly reduced and at best are prevented.

It is possible with the instrument according to the invention to introduce a laser probe 8 at the proximal end of the shank 2 (not shown) into the guide channel 4, and to displace it in the guide channel 4 in the axial direction so far, until the laser head 12 reaches the middle region 28 of the leaf spring 22, which projects into the guide channel 4. This middle region 28 first of all acts as an abutment which blocks a further axial movement of the laser probe 8 in the distal direction. By way of slightly increasing the axial pushing force onto the laser probe 8, the middle region 28 on account of its resilient design clears the cross section of the guide channel 4 to such an extent, that the laser head 12 may pass the narrowing formed by the middle region 28 of the leaf spring 22. As soon as the laser head 12 has passed the middle region 28, the deformation of the leaf spring 22 reforms back into its initial condition, and in this manner again reduces the clear diameter of the guide channel 4, until the middle region 28 of the leaf spring 22 comes to bear on the fiber lead 10 of the laser probe 8. On account of its bias, the leaf spring 22 thereby exerts a transverse force onto the fiber lead 10, which fixes the fiber lead transversely to its longitudinal extension, between the middle region 28 and the section of the inner wall of the guide channel 4, lying opposite this middle region 28. However, one ensures an axial movement ability of the fiber lead, so that this may be displaced distally so far, until the laser head 12 projects out of the shank 2 in its working position.

FIGS. 3 and 4 show a further design of the instrument according to the invention with a laser probe 8 arranged therein. With this embodiment too, a shank 2' forms a guide channel 4' for a laser probe 8, as well as a guide rail 6' for observation optics (not shown), directed parallel to the guide channel 4'. The laser probe 8 is shown in the working position in FIGS. 3 and 4, i.e., the laser head 12 of the laser probe 8 projects out of the distal end of the guide channel 4'.

Figure 2:
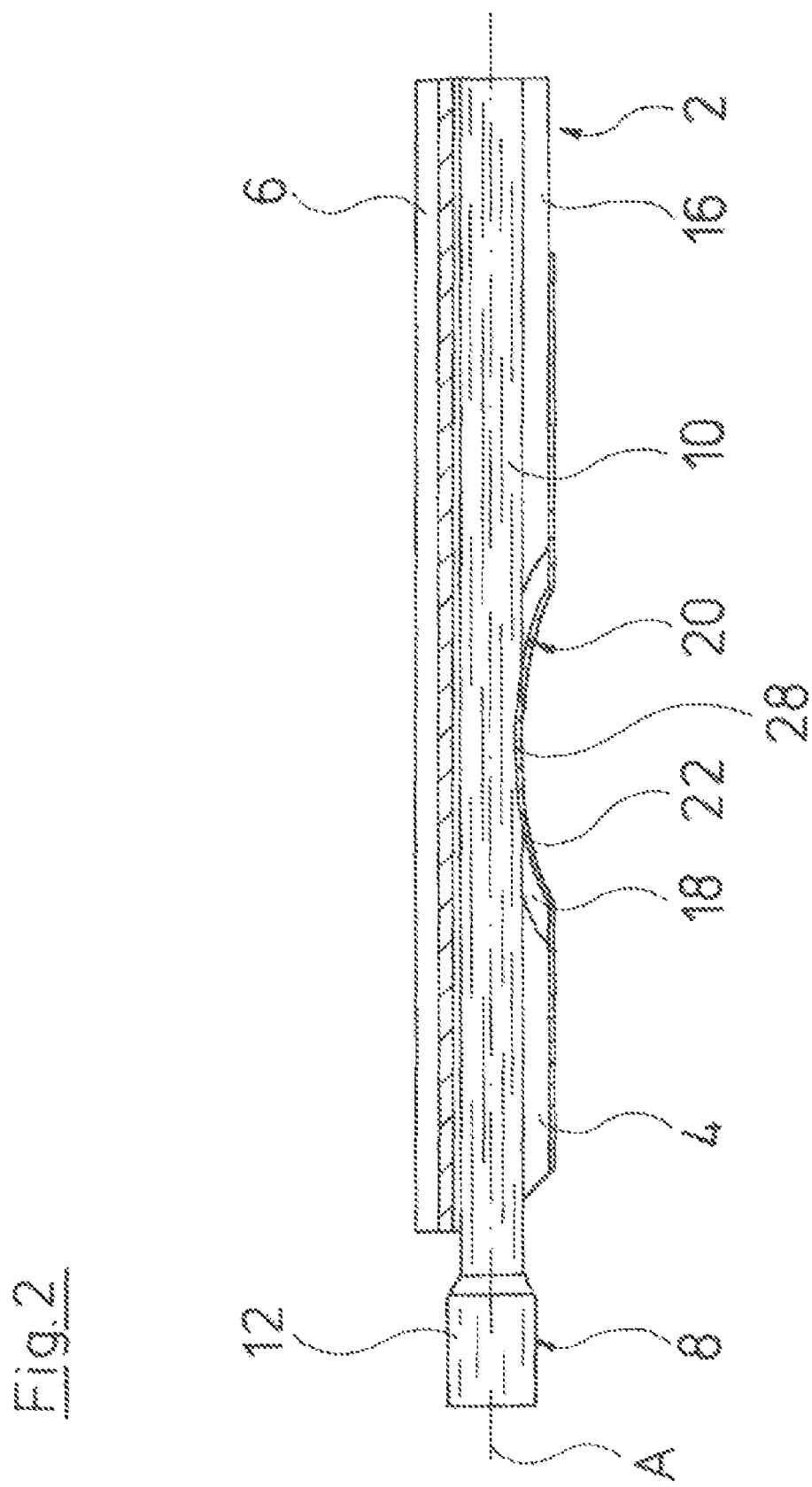
FIG. 2 a sectioned view of the distal end of a guide channel of the instrument according to FIG. 1.

In distinction to the design according to FIGS. 1 and 2, in the embodiment shown in FIGS. 3 and 4, a spring element 20' is formed itself by the wall 14' of the guide channel 4'. For this purpose, the wall 14' of the guide channel 4' is slotted in the longitudinal direction of the guide channel 4' in a manner such that two narrow, elongate openings 30 and 32 result. The openings 30 and 32 are aligned parallel to one another on the guide channel 4', and are spaced from one another by a section 34 of the wall 14'.

This section 34 of the wall 14' forms a spring element 20', wherein a middle section 28' is formed such that it engages convexly, and curved with a circular arc, into the inner lumen of the guide channel 4', and forms a narrowing there for fixing the fiber lead 10. The longitudinal extension of the curved middle section 28', which is significantly smaller compared to the length of the section 34 or of the openings 30 and 32, thereby permits a particularly favorable design of the spring element 20' formed by the section 34 of the wall 14', the design being resilient in the radial direction.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscopic instrument comprising a shank having at least one guide channel for a laser probe, and a flexible narrowing provided in a section of the guide channel proximate to a distal end of the guide channel, the flexible narrowing enabling a clear diameter of the guide channel to be changed in at least one direction.

2. The endoscopic instrument according to claim 1, wherein the flexible narrowing is provided by a spring element arranged on the guide channel.

3. The endoscopic instrument according to claim 2, wherein the spring element is formed by a section of a wall of the guide channel.

4. The endoscopic instrument according to claim 3, wherein the wall of the guide channel comprises two slotted openings directed essentially parallel to a longitudinal axis of the guide channel, and wherein the section of the wall of the guide channel, arranged between the openings, is curved in an arched manner such that it projects convexly into an inner lumen of the guide channel.

5. The endoscopic instrument according to claim 2, wherein the spring element comprises a leaf spring having two flat ends and a middle region curved in an arched manner between the two flat ends, the leaf spring being arranged such that the curved middle region, proceeding from an inner wall of the guide channel, projects convexly into an inner lumen of the guide channel.

6. The endoscopic instrument according to claim 5, wherein the wall of the guide channel comprises an opening through which the spring element is guided in a manner such that its curved middle region projects convexly into the inner lumen of the guide channel, and at least one flat end of the spring element is fastened on an outer wall of the guide channel.

7. The endoscopic instrument according to claim 5, wherein a plane of curvature of the spring element extends in a direction of the longitudinal axis of the guide channel.

8. The endoscopic instrument according to claim 1, comprising a working insert for a resectoscope.

9. An endoscopic instrument comprising: a shank defining a longitudinal axis extending from a proximal end to a distal end thereof; at least one guide channel formed by the shank, the at least one guide channel having an inner lumen sized and shaped for guiding a laser probe from the proximal end to the distal end of the shank; an opening extending through an exterior wall of the shank to the inner lumen of the at least one guide channel; and a spring element having a middle region curved in an arched manner in a relaxed state, the middle region extending into the inner lumen of the at least one guide channel.

10. The endoscopic instrument according to claim 9, wherein the middle region of the spring element is flexible permitting a change in shape of a cross section of the inner lumen for receipt of a laser probe.

11. The endoscopic instrument according to claim 9, wherein the spring element includes opposing end sections extending in a single plane, each end section of the spring element being attached to an exterior surface of the shank.

12. The endoscopic instrument according to claim 9, further comprising a handle arranged on a proximal end of the shank.

13. The endoscopic instrument according to claim 9, wherein a laser probe engages at least a portion of the middle region of the spring element.

* * * * *